United States Patent
Townsend et al.

(10) Patent No.: US 6,879,398 B2
(45) Date of Patent: Apr. 12, 2005

(54) DISTRIBUTED CONTAMINANT OPTICAL MONITORING SYSTEM

(75) Inventors: VanWinkle T. Townsend, Herndon, VA (US); Robert H. Fleming, Manassas, VA (US)

(73) Assignee: Lockheed Martin Corporation, Bethesda, MD (US)

( * ) Notice: Subject to any disclaimer, the term of this patent is extended or adjusted under 35 U.S.C. 154(b) by 289 days.

(21) Appl. No.: 10/152,756

(22) Filed: May 22, 2002

(65) Prior Publication Data

US 2003/0218748 A1 Nov. 27, 2003

(51) Int. Cl.$^7$ ............................................. G01N 15/02
(52) U.S. Cl. ...................................... 356/336; 356/339
(58) Field of Search ................................. 356/335–339

(56) References Cited

U.S. PATENT DOCUMENTS

| | | | |
|---|---|---|---|
| 3,406,289 A | 10/1968 | Schleusener | |
| 4,571,079 A | 2/1986 | Knollenberg | |
| 4,798,465 A | 1/1989 | Knollenberg | |
| 5,257,085 A | 10/1993 | Ulich et al. | |
| 5,557,415 A | 9/1996 | Nielsen et al. | |
| 5,642,193 A | 6/1997 | Girvin et al. | |
| 5,731,875 A | * | 3/1998 | Chandler et al. ............ 356/336 |
| 5,763,277 A | 6/1998 | Zhu et al. | |
| 5,767,967 A | * | 6/1998 | Yufa ............................ 356/336 |
| 5,813,987 A | 9/1998 | Modell et al. | |
| 5,866,430 A | 2/1999 | Grow | |
| 5,920,388 A | 7/1999 | Sandberg et al. | |
| 5,938,617 A | 8/1999 | Vo-Dinh | |
| 6,008,055 A | 12/1999 | Zhu et al. | |
| 6,025,200 A | 2/2000 | Kaish et al. | |
| 6,069,702 A | 5/2000 | Slater et al. | |
| 6,154,277 A | 11/2000 | Snelling et al. | |
| 6,181,419 B1 | 1/2001 | Snelling et al. | |
| 6,225,630 B1 | 5/2001 | Slater et al. | |

FOREIGN PATENT DOCUMENTS

WO    WO 98/11422    3/1998

* cited by examiner

*Primary Examiner*—Zandra V. Smith
(74) *Attorney, Agent, or Firm*—Simpson & Simpson, PLLC

(57) ABSTRACT

An apparatus for detecting particles in a sample of gas is disclosed. The apparatus comprises a single optical radiation source, a sensor head, and detection electronics. The sensor head comprises a housing having an elliptical cross section. The sensor head receives optical radiation from the source through a fiber optic line at the first focus, and a detector is located at the second focus. The detector receives radiation scattered and emitted by particles in the light beam at the first focus. The detection electronics determine the presence, and in one embodiment the identity, of particles based on the radiation incident on the detector.

17 Claims, 3 Drawing Sheets

DISTRIBUTED CONTAMINANT OPTICAL MONITORING SYSTEM

FIELD OF THE INVENTION

This invention relates to the detection of particles in a gas sample. More specifically it relates to a method and apparatus for the detection of atmospheric contaminants using optical radiation.

BACKGROUND OF THE INVENTION

The existence of particles in a gas sample is an ongoing concern for numerous applications. Particles in the atmosphere of a workplace can be a hazard to the employees. Particles in an electronics manufacturing facility can damage or destroy the components being manufactured. Nuclear, biological, or chemical (NBC) warfare agent particles are harmful to anyone who comes in contact with them. Methods and apparatus for detecting and identifying these particles have thus been developed to address these problems.

One method of detecting particles in a gas sample takes advantage of the well-known fact that particles in the atmosphere scatter optical radiation. In addition, some biological particles emit fluorescent radiation when they are excited by radiation at particular wavelengths. This has lead to the development of systems to detect and identify particles in a gas sample by measuring the radiation that the particles scatter and radiate when exposed to light. However, these systems have generally used long path optical beam systems to detect the particles. The particles scatter the incident radiation, and in some cases emit fluorescent radiation, in all directions. Typically, the light scattered and emitted substantially perpendicular to the source light path is measured. Existing detection systems place a single or multiple detectors around the sample area, only detecting the radiation that is scattered or emitted into a relatively small section of the total sphere. This forces the system to input a proportionally greater amount of radiation to ensure that a measurable level of scattered and emitted radiation reaches the detection electronics. This inefficiency has resulted in expensive detection systems that require a great deal of power to operate.

An example of such a system is disclosed in U.S. Pat. No. 5,920,388 (Sandberg et al.). This patent discloses an apparatus for detecting and identifying particles in a gas sample. The device disclosed uses a laser to irradiate a sensing region. Scattered and emitted light is received by detectors subtending a relatively small part of the unit sphere. Thus, the laser must be operated at a high power level to detect small concentrations of a substance. Further, the laser source can only irradiate one sample section, requiring a separate laser source for every sample area to be tested. This increases the size and cost of the detection system.

A device for counting particles is disclosed in U.S. Pat. No. 5,642,193 (Girvin et al.). The device is typically used to determine the air quality for industrial sites, such as clean rooms. The device comprises a laser with a sample volume in the path of the radiation. A single detector measures the intensity of the light scattered towards it. This patented device requires a high power level to ensure that enough light is scattered towards the detector, such that the detector can discriminate the scattered light over the noise level. Further, only one sample space can be irradiated, requiring a separate laser for each sample space to be tested.

U.S. Pat. No. 4,798,465 (Knollenberg) discloses a device for detecting the size of particles in a gas sample. The device disclosed is used to determine the contamination level of clean rooms. The structure of the device disclosed is similar to the structure of the device disclosed by Girvin et al. It has the same drawbacks: high cost and size, and the requirement of a separate laser source for each sample space to be measured.

Another example of a long path system is disclosed in U.S. Pat. No. 5,527,085 (Ulich et al.). This patent discloses a lidar system comprising a laser that irradiates a target and a telescope that receives backscattered and emitted radiation. The device then identifies the composition of the target based on the radiation received. This device can be mounted in an airplane and flown over a target. The distance to the target dramatically reduces the power received by the telescope, requiring a great deal of radiation to be emitted by the laser to achieve a measurable return at the telescope. As with the other apparatuses, each detection system requires a separate radiation source.

Clearly, then, there is a longfelt need for an apparatus that can detect particles in a gas sample that is lower in cost and size than long path optical detection systems.

SUMMARY OF THE INVENTION

The present invention comprises an apparatus for detecting particles in a sample of gas comprising a single optical radiation source, a sensor head, and detection electronics. The sensor head comprises a housing having an elliptical cross section. The sensor head receives optical radiation from the source through a fiber optic line at the first focus, and a detector is located at the second focus. The detector receives radiation scattered and emitted by particles in the light beam at the first focus. The detection electronics determine the presence, and in one embodiment the identity, of particles based on the radiation incident on the detector.

A general object of the present invention is to provide an apparatus for detecting atmospheric contaminants.

Another object of the present invention is to provide an apparatus wherein multiple detectors use a single optical source, to make the system smaller and lower in cost.

It is a further object to provide an apparatus that can detect the presence of environmental and industrial contaminants, as well as NBC warfare agents.

It is yet another object to provide an apparatus that can identify environmental and industrial contaminants, as well as NBC warfare agents.

These and other objects, features and advantages of the present invention will become readily apparent to those having ordinary skill in the art upon a reading of the following detailed description of the invention in view of the drawings and claims.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE PREFERRED EMBODIMENT

It should be appreciated that, in the detailed description of the invention which follows, like reference numbers on different drawing views are intended to identify identical structural elements of the invention in the respective views.

Figure 1:
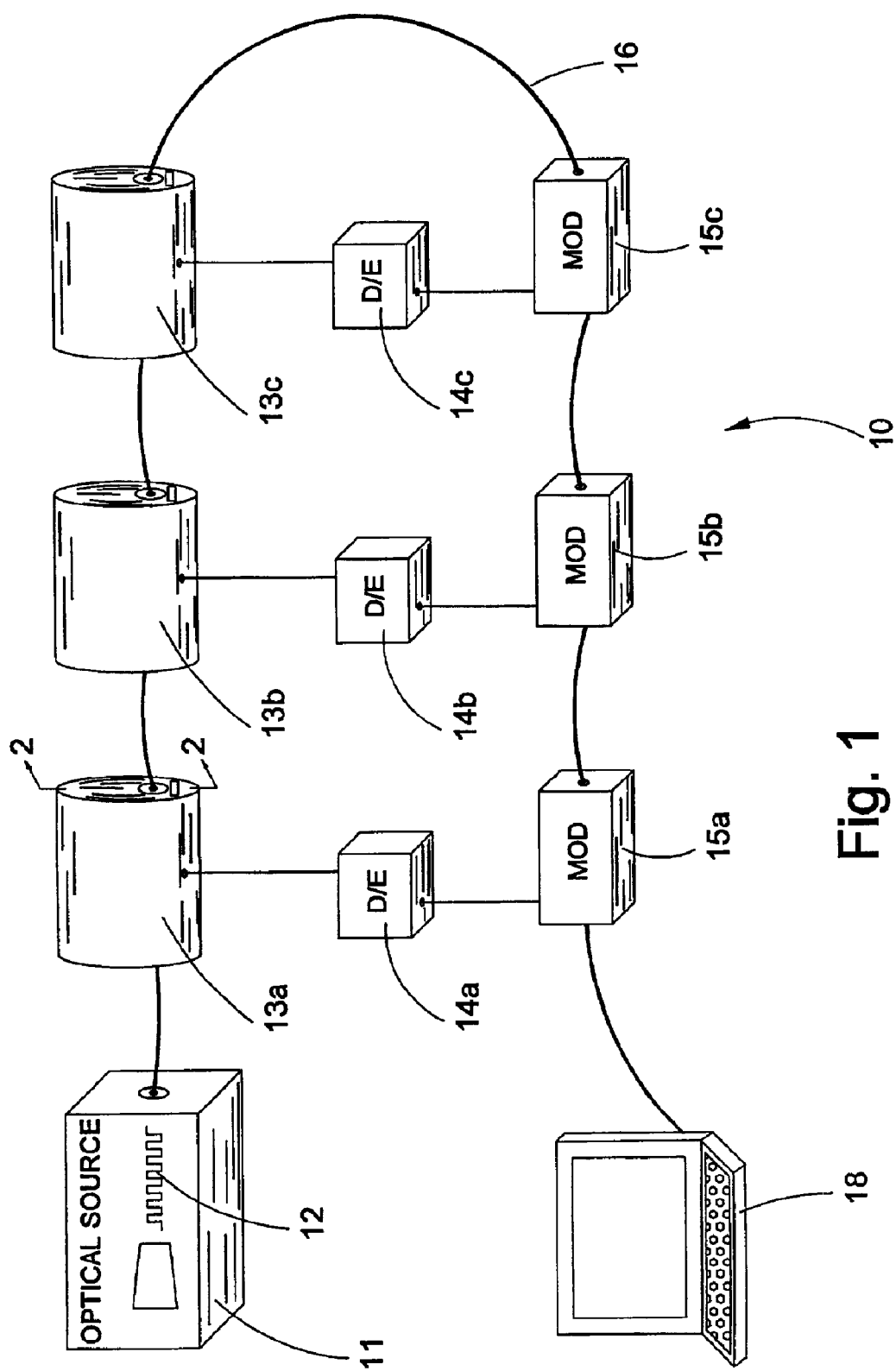
FIG. 1 is a perspective view of the preferred embodiment of the present invention.

The preferred embodiment of the present invention is shown in FIG. 1 and generally designated 10. The invention comprises a single optical source 11, at least one sensor head 13a, 13b, 13c, detection electronics 14a, 14b, 14c, respectively, for each of the sensor heads, a modulator 15a, 15b, 15c, respectively, for each of the sensor heads, a monitor 18, and a fiber optic line 16 that connects source 11, to each of sensor heads 13a, 13b, 13c, then to each of modulators 15a, 15b, 15c, and to monitor 18.

By utilizing a single optical source, the present invention is smaller in cost and size than other systems that use a different source for each detector. The optical source can be any optical radiation source from a light emitting diode (LED) to a tunable laser. In a preferred embodiment, the optical source provides square wave 12 with a frequency of 100 to 10,000 Hz and with a 50% duty cycle, to maximize detection performance at a low operating cost. It should be appreciated that other shape wave signals with other duty cycles and frequency ranges could be used.

Figure 2:
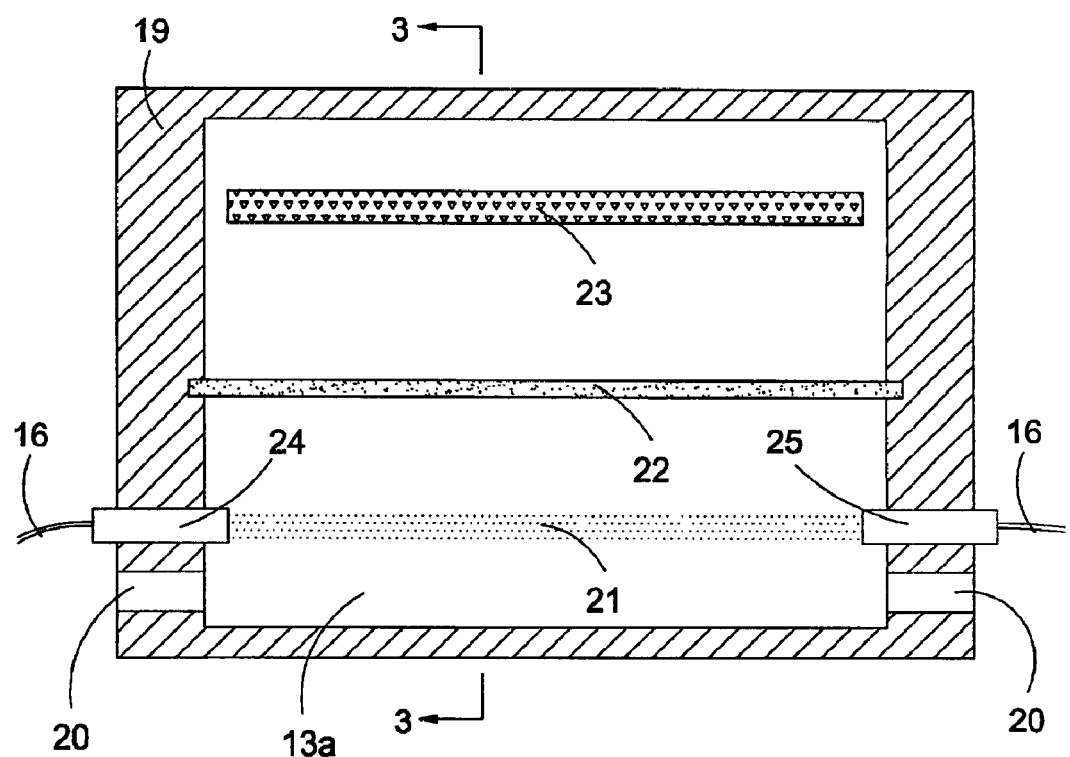
FIG. 2 is a front cross-sectional view of the sensor head of the preferred embodiment of the present invention, taken at plane 2—2 of FIG. 1.
Figure 3:
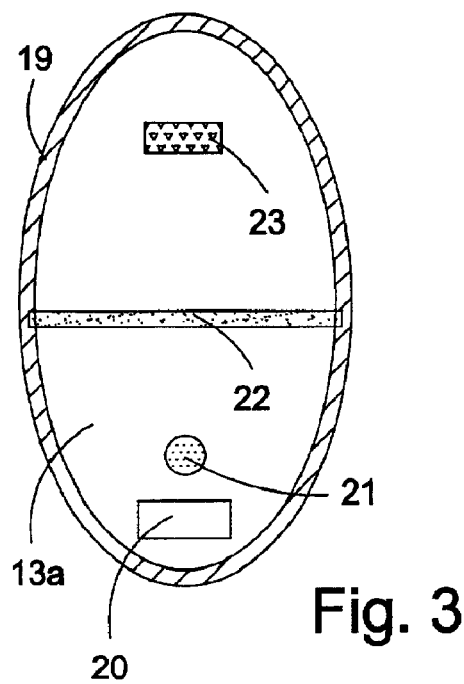
FIG. 3 is a side cross-sectional view of the sensor head of the preferred embodiment of the present invention, taken at plane 3—3 of FIG. 2; and, FIG. 4 is a perspective view of a second embodiment of the present invention.

A front cross sectional view of sensor head 13a is shown in FIG. 2. FIG. 3 is a side cross sectional view of the sensor head showing the elliptical cross section of sensor head housing 19. The interior of housing 19 is highly reflective of optical radiation. The radiation from source 11 travels down fiber optic line 16 to sensor head 13a. The radiation enters sensor head 13a through lens 24. Lens 24 expands the beam so that it has a larger cross section than that of line 16. This increases the volume that particles can be detected in. Lens 24 also collimates the light from line 16. This generates beam 21 that traverses the inside of sensor head 13a along one of the foci of the sensor head's elliptical cross section. The light in the expanded beam is scattered or absorbed by particles in the gas inside the sensor head. The particles may emit fluorescent radiation if they contain biological materials. Thus, scattered and emitted light travels through the inside of the sensor head. Detector 23 is located at the other focus of the sensor head housing. Light emitted or scattered from particles within beam 21 at all angles approximately perpendicular to the beam direction reflects off the inside of the elliptical cross section of the sensor head and arrives at the detector. This results in an efficient detection of the scattered and emitted radiation. The light that is not scattered or absorbed traverses the inside of the sensor head and reaches lens 25. Lens 25 collimates the incident light and reduces its cross section to that of fiber optic line 16. The light then continues down line 16. Light losses within the sensor head are small, allowing multiple sensor heads to be operated with a single optical radiation source.

In the preferred embodiment, vent 20 allows air from outside the sensor head to circulate through the sensor head. This allows continuous monitoring of the air quality of the area where the sensor head is mounted. However, the sensor heads may be closed to the ambient air, allowing detection of particles in a sample of gas introduced into the sensor head. This and other modifications should be readily apparent to one skilled in the art, and such modifications are within the spirit and scope of the invention as claimed. Also in a preferred embodiment, filter 22 may be mounted in housing 19 along its minor axis to physically isolate the detector from the outside air, and to narrow the bandwidth of the radiation that reaches the detector.

In a preferred embodiment, lenses 24 and 25 are gradient index (GRIN) lenses. However, it should be readily apparent to one skilled in the art that other means can be used to collimate and expand or reduce a beam, and these modifications are within the spirit and scope of the invention as claimed.

Detector 23 communicates with detection electronics 14. In a preferred embodiment, detector 23 comprises back-to-back planar arrays. Detection electronics 14 determine what substances are present based on the radiation incident on detector 23. All particles scatter light, and biological particles may emit fluorescent light when excited by incident radiation. The detection and identification of particles based on the scattering and emission of optical radiation is known in the art. The determination of particle size by the detection of optical radiation scattered and emitted from them is disclosed in U.S. Pat. No. 4,798,465, incorporated herein by reference. The identification of a substance by the detection of optical radiation scattered and emitted from it is disclosed in U.S. Pat. Nos. 5,257,085 and 5,938,617, both of which are incorporated herein by reference. Thus, the present apparatus can be configured to detect and identify environmental, industrial, and NBC warfare contaminants. However, it should be readily apparent to one skilled in the art that the present apparatus can be configured to simply detect the presence of any biological particle, any particle of a certain size range, any particles at all, or many other detection configurations. These modifications are intended to be within the spirit and scope of the invention as claimed.

Modulators 15 are in communication with detection electronics 14. The modulators receive the detection results from the corresponding sensor head. The modulators encode the results and transmit them down fiber optic line 16. Fiber optic line 16 traverses each of the modulators after it has traversed each of the sensor heads. Line 16 ends at monitor 18. Monitor 18 receives the detection information sent by the modulators down line 16. Monitor 18 decodes the detection information and displays it.

Figure 4:
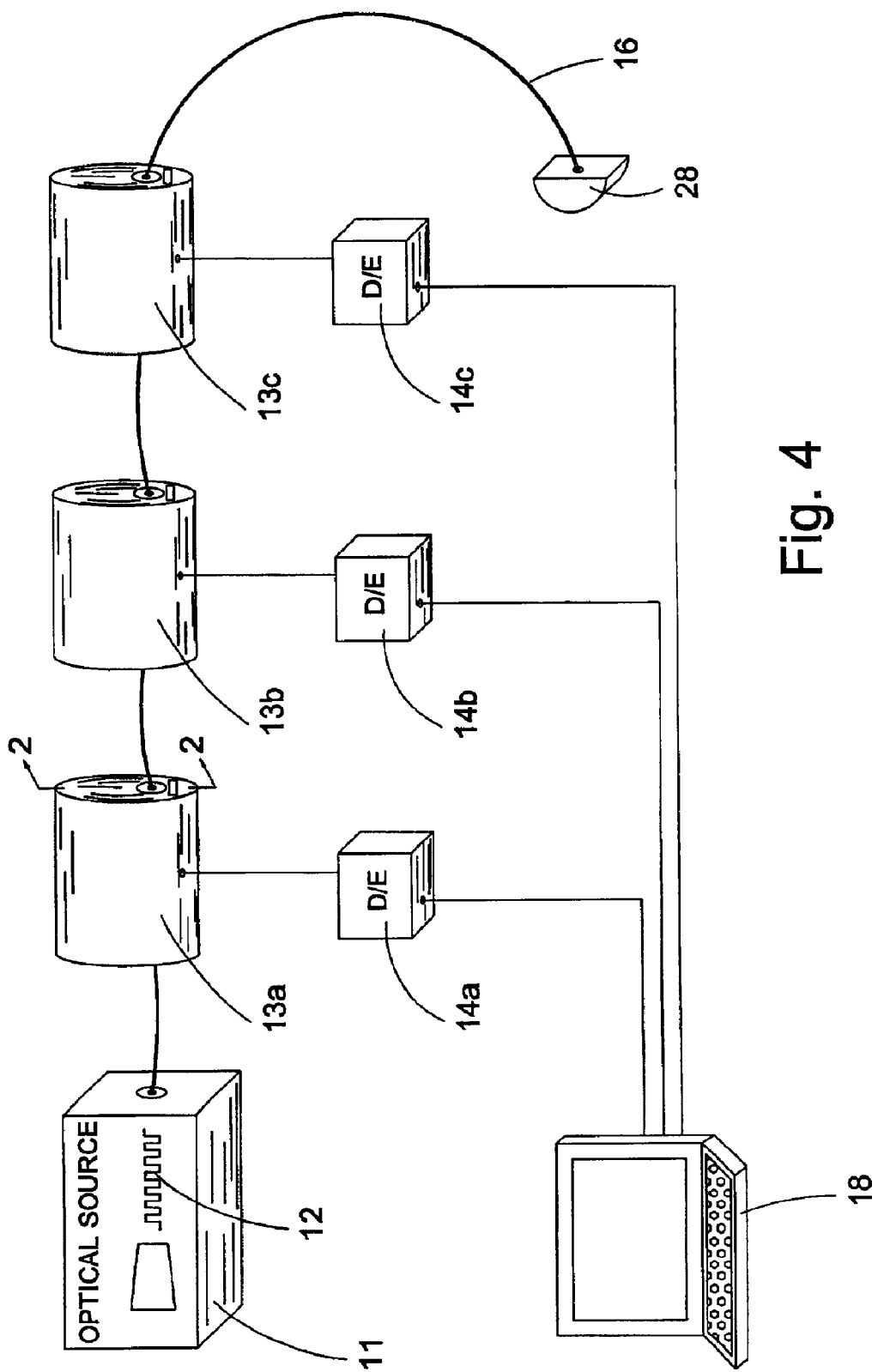

FIG. 4 shows an alternative embodiment. In this embodiment, fiber optic line 16 ends in optical trap 28. The detection electronics then directly communicate the detection results to the monitor. This modification is intended to be within the spirit and scope of the invention as claimed.

Thus, it is seen that the objects of the present invention are efficiently obtained, although modifications and changes to the invention should be readily apparent to those having ordinary skill in the art, and these modifications are intended to be within the spirit and scope of the invention as claimed.

What is claimed is:

1. An apparatus for detecting particles in a sample of gas comprising:

a single optical radiation source;

a sensor head, said sensor head having an elliptical cross section, said elliptical cross section having a first and a second focus, said sensor head operatively arranged to receive optical radiation from said source through a fiber optic line at said first focus, said sensor head having a detector located at said second focus, said detector operatively arranged to receive scattered and emitted radiation, said sensor head containing said sample of gas; and, a filter located in said sensor head between said first focus and said second focus.

2. An apparatus for detecting particles in a sample of gas comprising:

a single optical radiation source;

a sensor head, said sensor head having an elliptical cross section, said elliptical cross section having a first and a second focus, said sensor head operatively arranged to receive optical radiation from said source through a fiber optic line at said first focus, said sensor head having a detector located at said second focus, said detector operatively arranged to receive scattered and emitted radiation, said sensor head containing said sample of gas; and, a GRIN lens at an entrance to said sensor head, said lens operatively arranged to collimate and expand said source radiation.

3. An apparatus for detecting particles in a sample of gas comprising:

a single optical radiation source;

a sensor head, said sensor head having an elliptical cross section, said elliptical cross section having a first and a second focus, said sensor head operatively arranged to receive optical radiation from said source through a fiber optic line at said first focus, said sensor head having a detector located at said second focus, said detector operatively arranged to receive scattered and emitted radiation, said sensor head containing said sample of gas, and, a GRIN lens at an exit from said sensor head, said lens operatively arranged to collimate and reduce said source radiation.

4. An apparatus for detecting particles in a sample of gas comprising:

a single optical radiation source;

a sensor head, said sensor head having an elliptical cross section, said elliptical cross section having a first and a second focus, said sensor head operatively arranged to receive optical radiation from said source through a fiber optic line at said first focus, said sensor head having a detector located at said second focus, said detector operatively arranged to receive scattered and emitted radiation, said sensor head containing said sample of gas; and, a vent operatively arranged to allow air from outside said sensor head to circulate into said sample of gas contained in said sensor head.

5. An apparatus for detecting particles in a sample of gas comprising:

a single optical radiation source; and a plurality of sensor heads, each of said plurality of sensor heads having an elliptical cross section, each said elliptical cross section having a first and a second focus, said plurality of sensor heads operatively arranged to receive optical radiation from said source through one of a plurality of fiber optic lines, where each said head receives said optical radiation at its respective first focus, each of said plurality of sensor heads operatively arranged to transmit said radiation through an exit of each of said heads to one of said plurality of fiber optic lines to a subsequent sensor head, each of said plurality of sensor heads having a detector located at its respective second focus, each said detector operatively arranged to receive scattered and emitted radiation, each of said plurality of sensor heads containing said sample of gas.

6. The apparatus recited in claim 5 further comprising a plurality of means to determine a presence of particles in said sample of gas in communication with said detector of each of said plurality of sensor heads.

7. The apparatus recited in claim 5 further comprising a filter located in at least one of said plurality of sensor heads between said first and said second focus.

8. The apparatus recited in claim 5 further comprising a GRIN lens at an entrance to each of said plurality of sensor heads, said lens operatively arranged to collimate and expand said source radiation.

9. The apparatus recited in claim 5 further comprising a GRIN lens at an exit from each of said plurality of sensor heads, said lens operatively arranged to collimate and reduce said source radiation.

10. The apparatus recited in claim 5 further comprising a vent operatively arranged to allow air from outside said plurality of sensor heads to circulate into said sample of gas contained in said plurality of sensor heads.

11. The apparatus recited in claim 5 wherein said single optical source comprises an LED fiber optic transmitter.

12. The apparatus recited in claim 5 wherein said single optical source comprises a tunable laser.

13. The apparatus recited in claim 5 wherein said single optical source is operatively arranged to provide radiation at a frequency of 100 to 10,000 Hz and at a duty cycle of 50%.

14. The apparatus recited in claim 6 further comprising:

a plurality of modulators in communication with each of said detection means, said plurality of modulators operatively arranged to receive detection information from said detection means, said plurality of modulators operatively arranged to receive radiation in series from said source from one of said plurality of fiber optic lines after said radiation has traversed through all of said plurality of sensor heads, said plurality of modulators operatively arranged to encode said detection information in said received radiation; and a monitor, said monitor operatively arranged to receive radiation through one of said plurality of fiber optic links from said source after said radiation has traversed all of said plurality of modulators, said monitor operatively arranged to decode said detection information from said received radiation, and said monitor operatively arranged to display said detection information.

15. A method for detecting particles in a sample of gas comprising:

providing optical radiation from a single optical source;

transmitting said radiation through a fiber optic line to a sensor head having an elliptical cross section, said cross section having a first and a second focus, said sensor head containing said gas sample;

receiving said radiation at said first focus;

measuring radiation with a detector located at said second focus;

detecting particles in said gas sample based on said radiation received by said detector; and, transmitting in series said radiation through a plurality of fiber optic lines to a plurality of sensor heads.

16. The method recited in claim 15 further comprising:

transmitting said radiation in series to a plurality of modulators through one of said plurality of fiber optic lines after said radiation has traversed each of said plurality of sensor heads;

encoding said detection results; and transmitting said detection results to a monitor through one of said plurality of fiber optic lines.

17. The method recited in claim 16 wherein one of said plurality of modulators is associated with each of said plurality of sensor heads.

* * * * *